United States Patent
Philippe et al.

(10) Patent No.: US 7,396,897 B2
(45) Date of Patent: Jul. 8, 2008

(54) N-α- AND N-ε-LYSINE AND ORNITHINE COMPOUNDS COMPRISING A THIOL FUNCTION AND COSMETIC USE THEREOF

(75) Inventors: Michel Philippe, Wissous (FR); Hervé Andrean, Paris (FR)

(73) Assignee: L'Oreal S.A., Paris (FR)

( * ) Notice: Subject to any disclaimer, the term of this patent is extended or adjusted under 35 U.S.C. 154(b) by 850 days.

(21) Appl. No.: 10/821,914

(22) Filed: Apr. 12, 2004

(65) Prior Publication Data

US 2005/0019300 A1 Jan. 27, 2005

Related U.S. Application Data

(60) Provisional application No. 60/477,040, filed on Jun. 10, 2003.

(51) Int. Cl.
*C08G 69/10* (2006.01)
*C08G 63/08* (2006.01)

(52) U.S. Cl. .................. 528/328; 528/354; 528/373; 528/422; 424/70.17; 424/401

(58) Field of Classification Search ................. 528/328, 528/354, 373, 422; 424/70.17, 401
See application file for complete search history.

(56) References Cited

U.S. PATENT DOCUMENTS

| | | |
|---|---|---|
| 5,434,060 A | 7/1995 | Hiraki et al. |
| 6,395,867 B1 | 5/2002 | Maignan |
| 6,656,458 B1 | 12/2003 | Philippe et al. |

FOREIGN PATENT DOCUMENTS

| | | |
|---|---|---|
| JP | H08-217656 | 8/1996 |
| JP | 2000-509763 | 8/2000 |
| JP | 2001/328920 | 11/2001 |
| JP | 2002-509869 | 4/2002 |
| JP | 2002-293719 | 10/2002 |
| JP | 2002/293719 | 10/2002 |
| JP | 2003-40724 | 2/2003 |
| WO | WO 99/37279 | 7/1999 |

OTHER PUBLICATIONS

Database CA, Chemical Abstracts Service, Columbus, Ohio, US; Database Accession No. 84:65170, XP002267105.
Ashfaq Mahmood et al., "A New Approach to Labeling Cells with Technetium-99m, Part I. Preparation of Modified Polylysine and In Vitro Cell Labeling," Nuclear Medicine & Biology, vol. 23, 1996, pp. 79-85.
English language Derwent Abstract of JP 2001/328920, Nov. 27, 2001.
English language Derwent Abstract of JP 2002/293719, Oct. 9, 2002.
English Abstract for JP-H08-217656.
English Abstract for JP-2002-293719.
English Abstract for JP-2003-40724.
A. Mahmood et al., "A New Approach to Labeling Cells with Technetium-99m, Part I. Preparation of Modified Polylysine and In Vitro Cell Labeling," Nuclear Meddicine and Biology, vol. 23, No.1, pp. 79-85, 1996.

*Primary Examiner*—Duc Truong
(74) *Attorney, Agent, or Firm*—Finnegan, Henderson, Farabow, Garrett & Dunner, L.L.P.

(57) ABSTRACT

The present disclosure relates to the cosmetic use of poly-N-α- and -N-ε-lysine and ornithine compounds comprising a thiol function. The disclosure is also directed towards poly-N-α- and -N-ε-lysine and ornithine compounds comprising a thiol function and also to cosmetic compositions containing the disclosed compounds.

21 Claims, No Drawings

N-α- AND N-ε-LYSINE AND ORNITHINE COMPOUNDS COMPRISING A THIOL FUNCTION AND COSMETIC USE THEREOF

This application claims benefit of U.S. Provisional Application No. 60/477,040, filed Jun. 10, 2003.

The present disclosure relates to the cosmetic use of poly-N-α- and -N-ε-lysine and ornithine compounds comprising a thiol function. The disclosure is also directed towards poly-N-α- and -N-ε-lysine and ornithine compounds comprising a thiol function and also to cosmetic compositions containing the disclosed compounds.

Homooligomers and homopolymers based on polylysine (N-α and N-ε) are known in cosmetics, for example, in the context of fiber care (JP 2002 293 719) and of their antiseptic activity (JP 2001 328 920).

However, these compounds have ecotoxicity problems that greatly hinder their potential for application. It is also desirable to improve the remanence of these cationic polymers on the fiber.

Disclosed herein are polylysines that may form a remanent deposit on keratin materials, such as the hair, and that may also provide at least one good cosmetic property to keratin materials, such as the hair, for example, at least one good cosmetic property chosen from softness, smoothness, and better disentangling.

The present disclosure proposes a process for forming a remanent deposit on keratin materials, and for example, on keratin fibers, comprising applying to the keratin materials at least one compound of formula (I):

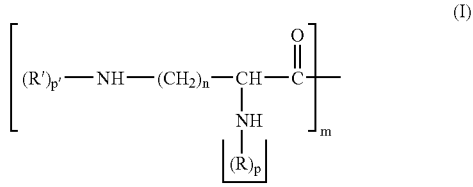

wherein:
n is 3 or 4,
P is different from P', P and P' are 0 or 1; and
wherein
when P' is 0, then the adjacent —NH group is engaged in an N-ε polymerization,
when P is 0, then the adjacent —NH group is engaged in an N-α polymerization; and
when P or P' is 1, then R or R' is chosen from A-SH, wherein
A is chosen from saturated and unsaturated, linear and branched C-1 to C-30 hydrocarbon-based chains optionally interrupted with at least one entity chosen from:
hetero atoms and functions, such as $NR_1$, O, S, S=O, O=S=O, Si, and C=O, wherein $R_1$ is chosen from hydrogen, alkyl(C-1 to C-8), acyl(C-1 to C-8), alkyl(C-1 to C-8)oxycarbonyl, alkyl(C-1 to C-8)aminocarbonyl, and halo radicals, and
aromatic and non-aromatic 5-, 6- or 7-membered rings optionally substituted with at least one group chosen from —COOH, —OH, —$NH_2$, alkyl(C-1 to C-8)amino, acyl(C-1 to C-8)amino, acyl(C-1 to C-8)oxy, alkyl(C-1 to C-8)oxycarbonylamino, alkyl(C-1 to C-8)aminocarbonyloxy, halo, and alkyl(C-1 to C-8)aminocarbonyl groups;

wherein R or R' may also be chosen from, in part, hydrogen,

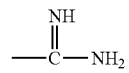

and the salts thereof, and

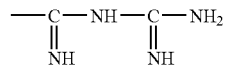

and the salts thereof;
A may also be chosen from 5-, 6- or 7-membered aromatic and non-aromatic rings, optionally substituted with at least one group chosen from —COOH, —OH, —$NH_2$, alkyl(C-1 to C-8)amino, acyl(C-1 to C-8)amino, acyl (C-1 to C-8)oxy, alkyl(C-1 to C-8)oxycarbonylamino, alkyl(C-1 to C-8)aminocarbonyloxy, halo, and alkyl (C-1 to C-8)aminocarbonyl groups; and
m ranges from 3 to 10,000.

For example, in the compound of formula (I), the degree of grafting with thiol function may be greater than or equal to 1%.

In addition, in the at least one compound of formula (I), for example, m may be greater than 5 and m may be less than 1,000.

The term "keratin material," as used herein, comprises the skin, the nails, and keratin fibers. The term "keratin fibers," as used herein, means head hair, the eyelashes, the eyebrows, and other hairs. The present disclosure is directed, for example, towards keratin fibers.

For the purposes of the present disclosure, the expression "remanent deposit on keratin fibers" means a continuous or non-continuous coating formed on a fiber, which remains present after at least one shampoo wash, for example, after five consecutive shampoo washes.

In the definition given above for the phrase "remanent deposit on keratin fibers," the coating may be chosen, from a chemical viewpoint, from polylysines according to the present disclosure, used alone or mixed with other cosmetically active compounds.

For the purposes of the present disclosure, the term "coating" means an envelope formed at the surface of each fiber, for example, head hair, after drying the cosmetic composition.

The abbreviation "poly-N-α- and -N-ε-lysine and ornithine" is used to denote, in combination, the derivatives poly-N-α-lysine, poly-N-α-ornithine, poly-N-ε-lysine and poly-N-ε-ornithine. The abbreviation "poly-N-ε-lysine and ornithine" is used to denote, in combination, the derivatives poly-N-ε-lysine and poly-N-ε-ornithine. The configuration of the lysine and the ornithine may be chosen from L and D enantiomers or a mixture of both L and D.

The "theoretical degree of grafting of thiol function" is defined herein as the theoretical percentage of lysine or ornithine units bearing the thiol function in the compound of formula (I).

In one embodiment, the compound of formula (I), i.e., the poly-N-α- and -N-ε-lysines and ornithines of formula (I) comprising a thiol function, may further comprise at least one conventional cosmetic active agent.

Once the at least one compound of formula (I) has been deposited on the keratin material, the highly cationic nature of the at least one compound may lead to good adhesion of conventional anionic cosmetic active agents, for example, dyes, conditioners, moisturizers, emollients or sunscreens.

However, these cosmetic active agents, when they are used alone, have very poor affinity for the keratin material.

In another aspect of the present disclosure, the at least one compound of formula (I) may have covalent reactivity, for example, with the hair via the formation of disulphide bonds. This covalent reactivity may further reinforce the value for obtaining a substantial remanence on the fiber material, compared with cationic polymers without thiol functions.

In a further aspect of the present disclosure, poly-N-α- and -N-ε-lysines and ornithines compounds of formula I may be used in combination with at least one conventional anionic cosmetic active agent, for example, dyes, conditioners, moisturizers, emollients, and sunscreens.

Also disclosed herein are compounds of formula (II), wherein said compounds are poly-N-ε- and poly-N-α-lysine and ornithine derivatives containing a thiol function:

$$\left[ (R')_{p'} - NH - (CH_2)_n - \underset{\underset{(R)_p}{NH}}{CH} - \overset{O}{\underset{}{C}} \right]_m$$
(II)

wherein n is 3 or 4,

P is different from P', P and P' are 0 or 1, and wherein
when P' is 0, then the adjacent —NH group is engaged in an N-ε polymerization,
when P is 0, then the adjacent —NH group is engaged in an N-α polymerization; and
when P or P' is 1, then R or R' is chosen from A'-SH
wherein A' is chosen from compounds of formula:

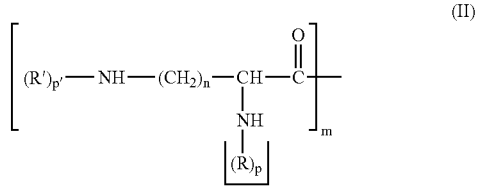

wherein $R_1$, $R_2$, $R_3$, and $R_4$, which may be identical or different, are chosen from hydrogen, and —COOH, —OH, —NH₂, alkyl(C-1 to C-8)amino, acyl(C-1 to C-8)amino, acyl(C-1 to C-8)oxy, alkyl(C-1 to C-8)oxycarbonylamino, alkyl(C-1 to C-8)aminocarbonyloxy, halo, and alkyl(C-1 to C-8)aminocarbonyl radicals;

wherein q ranges from 1 to 36, for example from 3 to 28, and further for example, from 5 to 26;

wherein R or R' may also be chosen from, in part:
hydrogen,

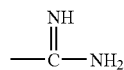

and salts thereof, and

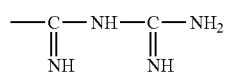

and salts thereof; and m ranges from 3 to 10,000.

For example, in the compound of formula (II), the degree of grafting of thiol function may be greater than or equal to 1%.

The present disclosure also relates to cosmetic compositions comprising, in a cosmetically acceptable medium, at least one compound of formula (II).

In the compositions in accordance with the disclosure, the at least one compound of formula (II) is, for example, present in an amount ranging from 0.05% to 30% by weight, for example, from 0.1% to 15% by weight, and further for example, from 0.25% to 10% by weight, relative to the total weight of the composition.

In accordance with yet another aspect of the disclosure, the composition may further comprise conventional cosmetic additives chosen from fixing polymers; thickeners; anionic, nonionic, cationic and amphoteric surfactants; fragrances; preserving agents; proteins; unreactive vitamins; unreactive provitamins; anionic, nonionic, cationic and amphoteric non-fixing polymers; mineral, plant and synthetic oils; volatile and non-volatile, linear and cyclic, modified and unmodified silicones; pH regulators; oxidizing agents; reducing agents; catalysts; and any other additive conventionally used in cosmetic compositions intended to be applied to keratin materials, for example, to the hair.

The cosmetically acceptable medium, for example, is chosen from water and at least one cosmetically acceptable solvent, such as alcohols, esters, ketones, cyclic volatile silicones, and water-solvent mixtures. These solvents, for example, may be chosen from $C_1$-$C_4$ alcohols.

When the composition disclosed herein is packaged in an aerosol device, the composition comprises at least one propellant, optionally chosen from volatile hydrocarbons such as n-butane, propane, isobutane, pentane, and halohydrocarbons. The propellant may also be chosen from carbon dioxide, nitrous oxide, dimethyl ether (DME), nitrogen, and compressed air. Mixtures of propellants may also be used. For example, the propellant may be dimethyl ether.

In one embodiment, the propellant is present in the composition in an amount ranging from 5% to 90% by weight, and for example, from 10% to 60% by weight, relative to the total weight of the composition in the aerosol device.

The compositions in accordance with the disclosure may be applied, for example, to dry or wet hair.

The compounds of formula (II), are prepared by reaction, under an inert atmosphere, for example, of poly-N-ε-lysine supplied, for example, by the company Chisso or of poly-N-ε-lysine containing a guanidine or biguanide function, with a thiolactone such as N-acetylhomocysteinethiolactone supplied, for example, by the company Fluka. The reaction time may, for example, range from 30 minutes to 24 hours. Further, the reaction temperature may range from 0° to 80° C. The polylysines may optionally be partially salified.

The composition of the disclosure may be for cosmetic or pharmaceutical use, such as for cosmetic use. Thus, the composition should comprise a non-toxic physiologically acceptable medium capable of being applied to the skin, the integuments, and the lips of human beings. For the purposes of the disclosure the term "cosmetic" means a composition of pleasant appearance, odor, and feel.

For example, the composition for application to the scalp or the hair may be in the form of a hair care lotion, for example, for daily or twice-weekly application, a shampoo or a hair conditioner, further for example, for twice-weekly or weekly application, a liquid or solid scalp cleansing soap for daily application, a product for shaping the hairstyle (lacquer, hair setting product or styling gel), a treatment mask, and a foaming gel or cream for cleansing the hair. The disclosed composition may also be in the form of a hair dye or hair mascara that may be applied with a brush or a comb.

Another aspect of the disclosure relates to the use of the compounds of formula (II), in cosmetics, applied, for example, to the skin, the nails, and/or keratin fibers.

For example, the compound of formula (II) may be present in a nail varnish, a skincare product, a makeup product, an anti-ageing product, or a hair-shaping, hair care or hair-coloring product.

The disclosure will be illustrated more fully with the aid of the non-limiting examples that follow.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES

Three polylysines of formula (II) and of L configuration in accordance with the invention, referred to as Examples 1, 2, and 3, were prepared.

Example 1

Structure (II)

n=4, p'=0, p=1,

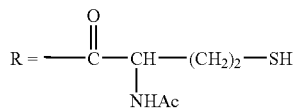

with a degree of grafting of 10% (residue R=H), mean m=37.

Example 2

Structure (II)

n=4, p'=0, p=1,

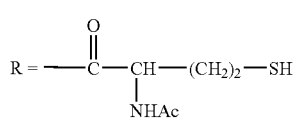

with a degree of grafting of 30% (residue R=H), mean m=37.

Example 3

Structure (II)

n=4, p'=0, p=1,

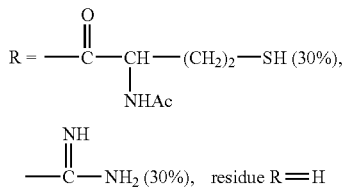

the structure being partially salified (HCl).

Synthesis of Example 1

25 g of an aqueous solution of polylysine from Chisso (containing 25% A.M., mean mass 4700) and 0.782 g of N-acetylhomocysteinethiolactone were placed in a reactor.

Procedure

The polylysine solution was degassed by sparging with argon.

The N-acetylhomocysteinethiolactone was added portion wise, waiting for the dissolution of the reagent between each addition, to the polylysine solution with stirring, at room temperature and under argon. The mixture was stirred under argon for 24 hours, while monitoring by Thin Layer Chromatography (TLC) ($CH_2Cl_2$/MeOH/$NH_3$ (15/4/1)) the disappearance of the reagent and the appearance of the thiol function on the polymer, which does not migrate, by revelation with sodium nitroprusside.

The $^{13}C$ nuclear magnetic resonance (NMR) analysis was in accordance with the expected structure.

Example 2 was prepared according to the same procedure as Example 1, increasing the amount of N-acetylhomocysteinethiolactone (2.35 g).

Remanence after 10 shampoo washes is observed for Examples 1 and 2.

Example 3: (Polylysine, 30% aminated and guanylated and 30% thiolated).

12 g of polylysine solution were partially salified with 0.5 ml of concentrated hydrochloric acid; after addition of 1.04 g of 1-H-pyrazolecarboxamidine monohydrochloride, the reaction medium was heated at 40° C. for 2 hours with stirring (the reaction was monitored by $^1H$ NMR).

After extraction of the pyrazole with ethyl ether and degassing under argon, 1.13 g of N-acetylhomocysteinethiolactone were added to the aqueous solution, still under argon; the mixture was stirred under argon at 40° C. for 16 hours (the reaction was monitored by NMR and TLC) and the pH of the solution was then brought to 5 by adding concentrated HCl.

The proton and $^{13}C$ NMR analyses were in accordance with the expected hydrochloride structure.

What is claimed is:

1. A compound of formula (II)

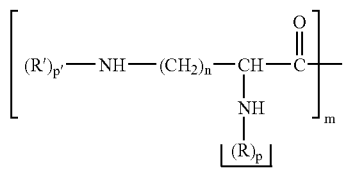
(II)

wherein:
n is 3 or 4,
P is different from P', and P and P' are 0 or 1,
wherein
when P' is 0, then the adjacent —NH group is engaged in an N-ε polymerization and
when P is 0, then the adjacent —NH group is engaged in an N-α polymerization; and
when P or P' is 1, then R or R' is A'-SH, wherein
A' is chosen from compounds of formula:

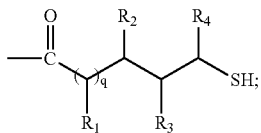

wherein $R_1$, $R_2$, $R_3$, and $R_4$, which may be identical or different, are chosen from hydrogen, and —COOH, —OH, —$NH_2$, alkyl(C-1 to C-8)amino, acyl(C-1 to C-8)amino, acyl(C-1 to C-8)oxy, alkyl(C-1 to C-8)oxycarbonylamino, alkyl(C-1 to C-8)aminocarbonyloxy, halo, and alkyl(C-1 to C-8)aminocarbonyl radicals;
wherein q ranges from 1 to 36;
wherein R or R' may also be chosen from hydrogen,

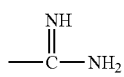

and salts thereof, and

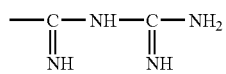

and salts thereof; and
m ranges from 3 to 10,000.

2. The compound according to claim 1, wherein the degree of grafting of thiol function is greater than or equal to 1%.

3. The compound according to claim 1, wherein q ranges from 3 to 28.

4. The compound according to claim 3, wherein q ranges from 5 to 26.

5. A cosmetic composition comprising, in a cosmetically acceptable medium, at least one compound of formula (II)

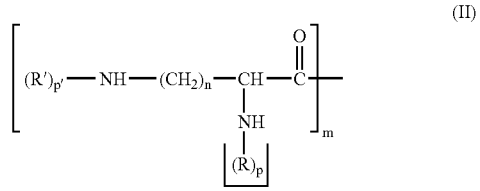
(II)

n is 3 or 4,
P is different from P', and P and P' are 0 or 1,
wherein
when P' is 0, then the adjacent —NH group is engaged in an N-ε polymerization and
when P is 0, then the adjacent —NH group is engaged in an N-α polymerization; and
when P or P' is 1, then R or R' is A'-SH, wherein
A' is chosen from

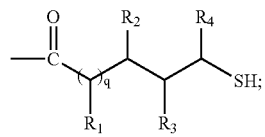

$R_1$, $R_2$, $R_3$, and $R_4$, which may be identical or different, are chosen from hydrogen, and —COOH, —OH, —$NH_2$, alkyl(C-1 to C-8)amino, acyl(C-1 to C-8)amino, acyl(C-1 to C-8)oxy, alkyl(C-1 to C-8)oxycarbonylamino, alkyl(C-1 to C-8)aminocarbonyloxy, halo, and alkyl(C-1 to C-8)aminocarbonyl radicals;
wherein q ranges from 1 to 36;
wherein R or R' may also be chosen from hydrogen,

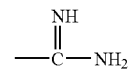

and salts thereof, and

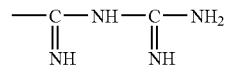

and salts thereof; and
m ranges from 3 to 10,000.

6. The composition according to claim 5, wherein the at least one compound of formula (II) is present in the composition in an amount ranging from 0.05% to 30% by weight, relative to the total weight of the composition.

7. The composition according to claim 6, wherein the at least one compound of formula (II) is present in the composition in an amount ranging from 0.1% to 15% by weight, relative to the total weight of the composition.

8. The composition according to claim 7, wherein at least one compound of formula (II) is present in the composition in an amount ranging from 0.25% to 10% by weight, relative to the total weight of the composition.

9. The composition according to claim 5, wherein the cosmetically acceptable medium is chosen from water and at least one cosmetically acceptable solvent.

10. The composition according to claim 9, wherein the at least one cosmetically acceptable solvent is chosen from alcohols, ketones, cyclic volatile silicones, and water-solvent mixtures.

11. The composition according to claim 10, wherein the at least one cosmetically acceptable solvent is chosen from C-1 to C-4 alcohols.

12. The composition according to claim 5, wherein the composition is housed in an aerosol device.

13. The composition according to claim 12, wherein the composition further comprises at least one propellant.

14. The composition according to claim 13, wherein the at least one propellant may be chosen from volatile hydrocarbons, carbon dioxide, nitrous oxide, dimethyl ether, nitrogen, and compressed air.

15. The composition according to claim 14, wherein the at least one propellant is present in an amount ranging from 5% to 90% by weight, relative to the total weight of the composition.

16. The composition according to claim 5, wherein q ranges from 3 to 28.

17. The composition according to claim 16, wherein q ranges from 5 to 26.

18. A process for preparing at least one compound of formula (II)

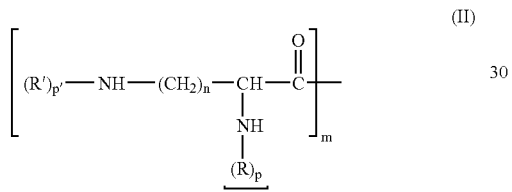

wherein
n is 3 or 4,
P is different from P', and P and P' are 0 or 1,
wherein,
when P' is 0, then the adjacent —NH group is engaged in an N-ε polymerization;
when P is 0, then the adjacent —NH group is engaged in an N-α polymerization; and
when P or P' is 1, then R or R' is A'-SH, wherein A' is chosen from compounds of formula:

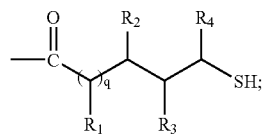

wherein $R_1$, $R_2$, $R_3$, and $R_4$, which may be identical or different, are chosen from hydrogen, and —COOH, —OH, —NH$_2$, alkyl(C-1 to C-8)amino, acyl(C-1 to C-8)amino, acyl(C-1 to C-8)oxy, alkyl(C-1 to C-8) oxycarbonylamino, alkyl(C-1 to C-8)aminocarbonyloxy, halo, and alkyl(C-1 to C-8)aminocarbonyl radicals;

q ranges from 1 to 36;
wherein R or R' may also be chosen from
hydrogen,

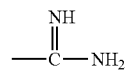

and salts thereof, and

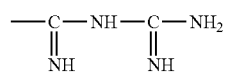

and salts thereof; and
m ranges from 3 to 10,000,
comprising reacting, under an inert atmosphere, of poly-N-ε-lysine or poly-N-ε-lysine containing a guanidine or biguanide function with a thiolactone.

19. The process according to claim 18, wherein the thiolactone is chosen from N-acetylhomocysteinethiolactone.

20. The process according to claim 18, wherein q ranges from 3 to 28.

21. The process according to claim 20, wherein q ranges from 5 to 26.

* * * * *